United States Patent
Boday et al.

(10) Patent No.: US 9,981,932 B2
(45) Date of Patent: May 29, 2018

(54) BIODERIVED BASED PLASTICIZERS

(71) Applicant: International Business Machines Corporation, Armonk, NY (US)

(72) Inventors: Dylan J. Boday, Tucson, AZ (US); Joseph Kuczynski, North Port, FL (US); Jason T. Wertz, Poughkeepsie, NY (US); Jing Zhang, Poughkeepsie, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days. days.

(21) Appl. No.: 15/396,755

(22) Filed: Jan. 2, 2017

(65) Prior Publication Data
US 2017/0107191 A1    Apr. 20, 2017

Related U.S. Application Data

(60) Division of application No. 14/728,081, filed on Jun. 2, 2015, which is a continuation of application No. 14/636,336, filed on Mar. 3, 2015, now Pat. No. 9,518,167.

(51) Int. Cl.
*C07D 307/42* (2006.01)
*C08K 5/1535* (2006.01)
*C08K 5/00* (2006.01)

(52) U.S. Cl.
CPC .......... *C07D 307/42* (2013.01); *C08K 5/1535* (2013.01); *C08K 5/0016* (2013.01)

(58) Field of Classification Search
CPC ............................ C07D 307/42; C08K 5/1535
See application file for complete search history.

(56) References Cited

U.S. PATENT DOCUMENTS

| | | | |
|---|---|---|---|
| 4,218,386 A | 8/1980 | Logan et al. | |
| 7,842,761 B2 | 11/2010 | Flynn et al. | |
| 9,139,689 B1 | 9/2015 | Flynn et al. | |
| 9,518,167 B2 | 12/2016 | Boday et al. | |
| 2007/0203276 A1 | 8/2007 | Fenyvesi et al. | |
| 2009/0018300 A1 | 1/2009 | Bloom et al. | |
| 2012/0181058 A1 | 7/2012 | Chaudhary et al. | |
| 2012/0214920 A1 | 8/2012 | Frenkel | |
| 2012/0220507 A1 | 8/2012 | Grass et al. | |
| 2013/0023608 A1 | 1/2013 | Kellett et al. | |
| 2013/0087073 A1 | 4/2013 | Mullen et al. | |
| 2013/0236937 A1 | 9/2013 | Harlin et al. | |
| 2013/0239852 A1 | 9/2013 | Davies et al. | |
| 2014/0027945 A1 | 1/2014 | Alidedeoglu et al. | |
| 2014/0069299 A1 | 3/2014 | Becker et al. | |
| 2014/0088233 A1 | 3/2014 | Kann | |
| 2016/0257803 A1 | 9/2016 | Boday et al. | |
| 2016/0257804 A1 | 9/2016 | Boday et al. | |
| 2017/0044352 A1 | 2/2017 | Storzum et al. | |

FOREIGN PATENT DOCUMENTS

WO    2011023590A1 A1    3/2011

OTHER PUBLICATIONS

Vijayendran, "Biobased Chemicals: Technology, Economics and Markets," downloaded from <http://www.nova-institut.de/pdf/11-01%20Biobased%20Chemicals%20White%20Paper%20Asia.pdf> on Jan. 8, 2015.
List of IBM Patents or Patent Applications Treated as Related (Dated Jan. 2, 2017).
U.S. Appl. No. 14/728,081, to Dylan J. Boday et al., entitled "Bioderived Based Plasticizers", filed Jun. 2, 2015, assigned to International Business Machines Corporation.
U.S. Appl. No. 14/636,336, to Dylan J. Boday et al., entitled "Bioderived Based Plasticizers", filed Mar. 3, 2015, assigned to International Business Machines Corporation.

*Primary Examiner* — Golam M Shameem
(74) *Attorney, Agent, or Firm* — Matthew J. Bussan

(57) ABSTRACT

A bioderived based plasticizer is produced by reacting a bioderived diol (and/or a bioderived alcohol) and a bioderived carboxylic acid in the presence of N,N'-dicyclohexylcarbodiimide (DCC), wherein the bioderived carboxylic acid includes a hydrolyzed oil. The bioderived carboxylic acid (e.g., linoleic acid, α-linolenic acid, oleic acid, and mixtures thereof) may be produced by hydrolyzing a triglyceride, such as canola oil, linseed oil, soybean oil, and mixtures thereof. In one embodiment of the present invention, a bioderived based plasticizer is produced by reacting 2,5-bis-(hydroxymethyl)furan and α-linolenic acid in the presence of DCC. In some embodiments of the present invention, the bioderived based plasticizer is blended into one or more polymers.

12 Claims, 1 Drawing Sheet

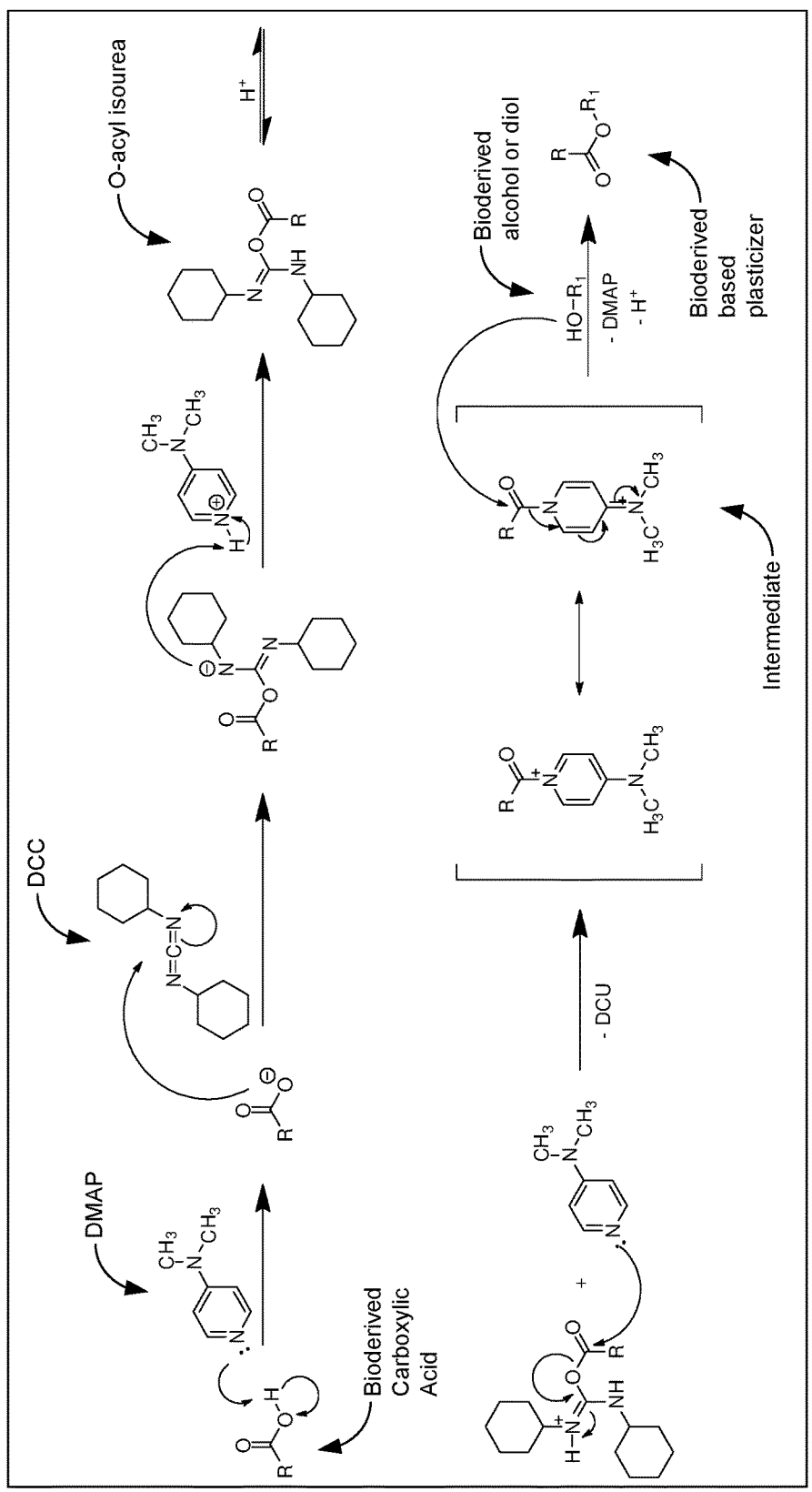

BIODERIVED BASED PLASTICIZERS

CROSS-REFERENCE TO RELATED APPLICATION

This patent application is a divisional application of pending U.S. patent application Ser. No. 14/728,081, filed Jun. 2, 2015, entitled "BIODERIVED BASED PLASTICIZERS", which is a continuation application of U.S. patent application Ser. No. 14/636,336, filed Mar. 3, 2015, entitled "BIODERIVED BASED PLASTICIZERS" (now U.S. Pat. No. 9,518,167), each of which is hereby incorporated herein by reference in its entirety.

BACKGROUND

The present invention relates in general to plasticizers. More particularly, the present invention relates to plasticizers based on bioderived feedstocks. The present invention also relates to a method for producing such bioderived based plasticizers, as well as to articles of manufacture employing such bioderived based plasticizers.

SUMMARY

In accordance with some embodiments of the present invention, a bioderived based plasticizer is produced by reacting a bioderived diol (and/or a bioderived alcohol) and a bioderived carboxylic acid in the presence of N,N'-dicyclohexylcarbodiimide (DCC), wherein the bioderived carboxylic acid includes a hydrolyzed oil. The bioderived carboxylic acid (e.g., linoleic acid, α-linolenic acid, oleic acid, and mixtures thereof) may be, for example, produced by hydrolyzing a triglyceride, such as canola oil, linseed oil, soybean oil, and mixtures thereof. In one embodiment of the present invention, a bioderived based plasticizer is produced by reacting 2,5-bis(hydroxymethyl)-furan and α-linolenic acid in the presence of DCC. In some embodiments of the present invention, the bioderived based plasticizer is blended into one or more polymers.

BRIEF DESCRIPTION OF THE DRAWING

Embodiments of the present invention will hereinafter be described in conjunction with the appended drawing, where like designations denote like elements.

FIG. 1 is a chemical reaction diagram showing a detailed reaction mechanism for reacting a bioderived carboxylic acid and a bioderived alcohol or diol in the presence of N,N'-dicyclohexylcarbodiimide (DCC) to produce a bioderived based plasticizer in accordance with some embodiments of the present invention.

DETAILED DESCRIPTION

The use of plasticizers within materials is important for increasing the plasticity of a given material. Plasticizers are used within a myriad of materials such as polymers, concrete, clays, etc. In polymers, for example, it is not uncommon for phthalic acid diesters (also known as "phthalates") to be used as a plasticizer to impart softness and flexibility. This is especially the case in hard, brittle plastics like polyvinyl chloride (PVC). To produce a plasticized PVC, the PVC is blended with plasticizers, most commonly esters of phthalic acid, such as butyl benzyl phthalate (BBP), di-2-ethylhexyl phthalate (DEHP), diisononyl phthalate (DINP) and diisodecyl phthalate (DIDP). A major problem with the use of this common group of plasticizers is their potential toxicity when released from the polymer through biodegradation, photodegradation, anaerobic degradation, and the like. Due to this concern, there is a shift away from phthalate-based plasticizers to bioderived plasticizers that hold the potential to be less toxic to humans and the environment. Additionally, plasticizers based on bioderived materials reduce our dependency on petroleum sources which have come under scrutiny due to the long-term increased cost of petroleum and sustainability concerns.

In accordance with some embodiments of the present invention, a bioderived based plasticizer is produced by reacting a bioderived diol (and/or a bioderived alcohol) and a bioderived carboxylic acid in the presence of N,N'-dicyclohexylcarbodiimide (DCC), wherein the bioderived carboxylic acid includes a hydrolyzed oil. DCC (CAS number 538-75-0) is a commercially available dehydrating agent.

The bioderived diol utilized to produce a bioderived based plasticizer in accordance with some embodiments of the present invention may be any suitable diol prepared from renewable material. Suitable bioderived diols include, without limitation, 2,5-bis(hydroxymethyl)furan, 2,5-bis(hydroxymethyl)tetrahydrofuran, isosorbide, isomannide, isoidide, maltitol, maltitol syrup, lactitol, isomalt, 1,3-propanediol, 1,4-butanediol, mannitol, xylitol, erythritol, a diol produced from the hydrogenation of a hydroformylated fatty acid, a diol produced from the hydrogenation of an epoxidized fatty acid or epoxidized fatty acid alcohol, a diol produced from the reduction of an α,ω-dicarboxylic acid, and mixtures of any thereof. Derivatives of one or more of the above-listed suitable bioderived diols may also be utilized. Additional details regarding bioderived diols and their preparation are disclosed in U.S. Patent Application Publication No. 2009/0018300 A1, which is hereby incorporated herein by reference in its entirety.

Preferred bioderived diols that may be utilized to produce a bioderived based plasticizer in accordance with some embodiments of the present invention include, but are not limited to, 2,5-bis(hydroxymethyl)furan (CAS number 1883-75-6), 2,5-bis(hydroxymethyl)tetrahydrofuran (CAS number 104-80-3), and isosorbide (CAS number 652-67-5), each of which is commercially available.

Although not preferred, a bioderived alcohol may be used in lieu of, or in addition to, the bioderived diol to produce a bioderived based plasticizer in accordance with some embodiments of the present invention. In this regard, any suitable alcohol prepared from renewable material may be utilized. Suitable bioderived alcohols include, without limitation, hydroxymethylfurfural, furfuryl alcohol, tetrahydrofurfuryl alcohol, and mixtures thereof.

The bioderived carboxylic acid utilized to produce a bioderived based plasticizer in accordance with some embodiments of the present invention may be any suitable carboxylic acid prepared from renewable material. Suitable bioderived carboxylic acids include, without limitation, linoleic acid, α-linolenic acid, oleic acid, and mixtures of any thereof. Suitable bioderived carboxylic acids may be, for example, produced by hydrolyzing a triglyceride, such as canola oil, linseed oil (also known as "flaxseed oil"), soybean oil, and mixtures thereof. Other triglycerides (besides those just described) that may be hydrolyzed to produce suitable bioderived carboxylic acids include, without limitation, coconut oil, lard, olive oil, palm oil, palm kernel oil, peanut oil, rapeseed oil (other than canola oil, which was described earlier), safflower oil, sesame oil, sunflower oil and tallow. Alternatively, suitable bioderived carboxylic acids may be purchased commercially.

The synthetic techniques utilized in the hydrolysis of triglycierides to produce bioderived carboxylic acids are well known in the art. Typically, a triglyceride reactant having its carboxylic acid moieties containing from 6 to 26 carbon atoms is reacted with water in the presence of low molecular weight displacing acid catalyst, strong acid catalyst, and sufficient water to form oil and water phases, to produce bioderived carboxylic acids corresponding to the above-mentioned moieties and glycerine. The triglyceride reactant can be a specific triglyceride. However, the triglyceride is usually a mixture of different triglycerides which are naturally occurring fats and oils. Additional details regarding the preparation of bioderived carboxylic acids through hydrolysis of triglycerides are disclosed in U.S. Pat. No. 4,218,386, which is hereby incorporated herein by reference in its entirety.

Preferred bioderived carboxylic acids that may be utilized to produce a bioderived based plasticizer in accordance with some embodiments of the present invention include, but are not limited to, a hydrolyzed oil having a chemical structure represented by the following formula:

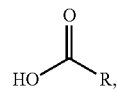

wherein R is aliphatic, can be saturated or unsaturated, and contains from 5 to 25 carbon atoms. The unsaturated moieties are usually mono-, di-, or tri-unsaturated. Such preferred bioderived carboxylic acids include, for example, linoleic acid (CAS number 60-33-3), α-linolenic acid (CAS number 463-40-1), and oleic acid (CAS number 112-80-1), each of which is commercially available.

In one embodiment of the present invention, described below, 2,5-bis(hydroxymethyl)furan and α-linolenic acid are reacted in the presence of DCC to produce a bioderived based plasticizer having a chemical structure represented by the following formula:

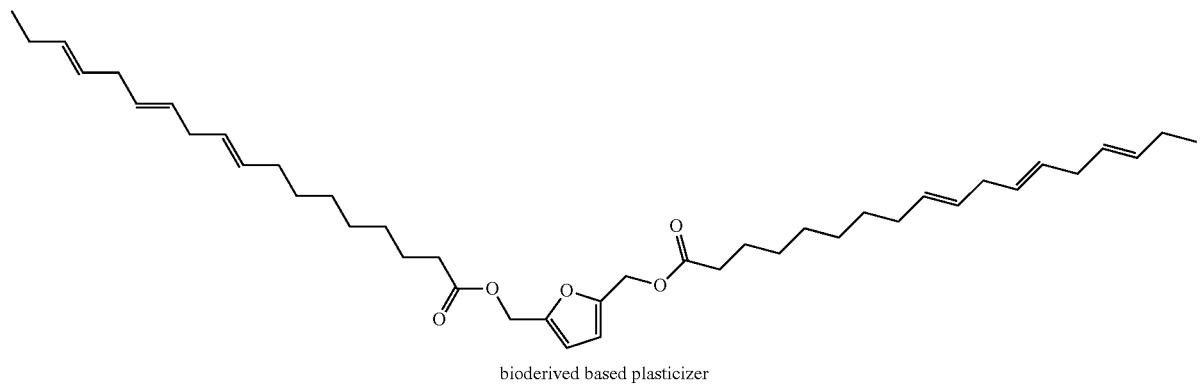 [SMILES: CC/C=C/C/C=C/C/C=C/CCCCCCCC(=O)OCc1ccc(COC(=O)CCCCCCC/C=C/C/C=C/C/C=C/CC)o1]

bioderived based plasticizer

In the just described embodiment of the present invention, the bioderived based plasticizer molecule is made symmetrical by reacting the same bioderived carboxylic acid (i.e., α-linolenic acid) on both sides of the bioderived diol (i.e., 2,5-bis(hydroxymethyl)furan). Alternatively, a bioderived based plasticizer molecule in accordance with other embodiments of the present invention may be asymmetrical by reacting different bioderived carboxylic acids on the respective sides of the bioderived diol.

A bioderived based plasticizer in accordance with some embodiments of the present invention may be used within polymers, such as PVC. The bioderived based plasticizer may be blended into an admixture with one or more polymers in a manner similar to conventional plasticizers. This would allow the industry to shift away from known toxic plasticizers towards more environmentally friendly material.

Reaction Scheme 1, described below, is a synthetic example of a reaction scheme that may be utilized to synthesize a bioderived based plasticizer in accordance with some embodiments of the present invention. In the first step of Reaction Scheme 1, linseed oil is reacted under acid hydrolysis conditions forming a hydrolyzed oil (i.e., linoleic acid, α-linolenic acid, and oleic acid). In the second step of Reaction Scheme 1, a bioderived diol in the form of 2,5-bis(hydroxymethyl)furan is reacted with a bioderived carboxylic acid in the form of the hydrolyzed oil from the first step of Reaction Scheme 1 (for the sake of simplicity, only α-linolenic acid is shown in the second step) in the presence of N,N'-dicyclohexylcarbodiimide (DCC) to form a bioderived based plasticizer.

to the above-mentioned moieties and glycerine (not shown). A prophetic example of the first step of Reaction Scheme 1 is set forth below.

In the first step of Reaction Scheme 1, linseed oil is an exemplary triglyceride reactant. One skilled in the art will appreciate that any suitable triglyceride reactant may be hydrolyzed in the first step of Reaction Scheme 1 in lieu of, or in addition to, linseed oil.

In the second step of Reaction Scheme 1, a bioderived diol (i.e., 2,5-bis(hydroxymethyl)furan) is reacted with a bioderived carboxylic acid (i.e., the hydrolyzed oil from the Reaction Scheme 1

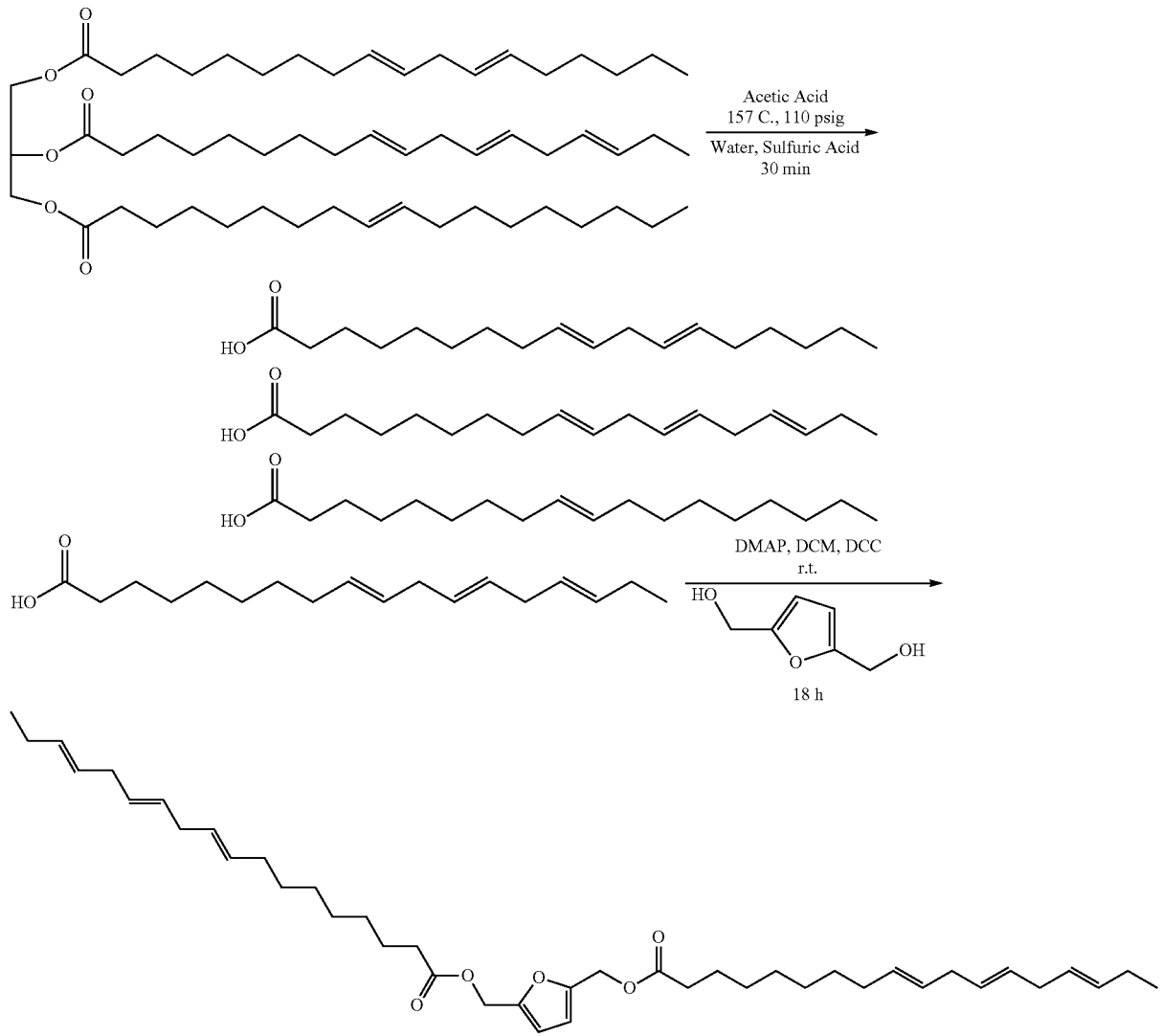

Thus, in accordance with some embodiments of the present invention, a bioderived based plasticizer, which is 100% bio-based, is synthesized in two steps. Advantageously, high yield is achieved due to minimal processing steps.

In the first step of Reaction Scheme 1, linseed oil is reacted with water in the presence of low molecular weight displacing acid catalyst (i.e., acetic acid), strong acid catalyst (i.e., sulfuric acid), and sufficient water to form oil and water phases, to produce bioderived carboxylic acids (i.e., linoleic acid, α-linolenic acid, and oleic acid) corresponding first step of Reaction Scheme 1—only the α-linolenic acid produced in the first step is shown in the second step for the sake of simplicity) in the presence of N,N'-dicyclohexylcarbodiimide (DCC) to form a bioderived based plasticizer in accordance with some embodiments of the present invention. A significant benefit of using DCC, as discussed below with reference to the detailed reaction mechanism shown in FIG. 1, is that the water released in the coupling of the ester to the bioderived alcohol or diol is captured in dicyclohexylurea (DCU), thereby making the workup easier and enhancing the yield. A prophetic example of the second step of Reaction Scheme 1 is set forth below.

In the second step of Reaction Scheme 1, α-linolenic acid is an exemplary bioderived carboxylic acid and 2,5-bis(hydroxymethyl)furan is an exemplary bioderived diol. One skilled in the art will appreciate that any suitable bioderived carboxylic acid(s) may be used in the second step of Reaction Scheme 1 in lieu of, or in addition to, α-linolenic acid. Likewise, one skilled in the art will appreciate that any suitable bioderived diol (and/or any suitable bioderived alcohol) may be used in the second step of Reaction Scheme 1 in lieu of, or in addition to, 2,5-bis(hydroxymethyl)-furan.

Prophetic Example of Reaction Scheme 1

First Step.

To a 2 L agitation vessel, linseed oil (400 g) and acetic acid (700 g) are added. The mixture is then heated to 157° C. from ambient and pressurized to 110 psig. To the heated and pressurized mixture, water (47 g) and sulfuric acid (11.5 g) are added. The reaction is then allowed to proceed for 30 min at 157° C. and 110 psig. After reaction, the mixture is cooled to room temperature (r.t.) and depressurized, followed by purification using techniques well known in the art.

Second Step.

Some of the hydrolyzed oil synthesized in the first step (2.5 equiv) and 4-(dimethylamino)pyridine (DMAP) (0.2 equiv) in dichloromethane (DCM) is added with N,N'-dicyclohexylcarbodiimide (DCC) (2.2 equiv) to a stirred solution at room temperature (r.t.). Once dissolved, 2,5-bis(hydroxymethyl)furan (1.0 equiv) is added and stirred for 18 h. The reaction mixture is then diluted with DCM and washed with 1.0 M aq. HCl, sat. aq. NaHCO₃ solution and brine, followed by drying over MgSO₄, and concentrated in vacuo to yield crude plasticizer. Further purification can be done using techniques well known in the art. *End of Prophetic Example of RS1*

FIG. 1 is a chemical reaction diagram showing a detailed reaction mechanism for reacting a bioderived carboxylic acid and a bioderived alcohol or diol in the presence of N,N'-dicyclohexylcarbodiimide (DCC) to produce a bioderived based plasticizer in accordance with some embodiments of the present invention. In FIG. 1, for the sake of simplicity, a bioderived alcohol is shown in lieu of a bioderived diol. As mentioned above, a significant benefit of using DCC is that the water released in the coupling of the ester to the bioderived alcohol or diol is captured in dicyclohexylurea (DCU), thereby making the workup easier and enhancing the yield.

The bioderived carboxylic acid (through deprotonation via interaction with DMAP) reacts with DCC to form an O-acyl isourea, which is more reactive than the free acid. The O-acyl isourea reacts with DMAP, forming DCU and an intermediate. The bioderived alcohol or diol attacks the intermediate, forming DMAP and the corresponding ester (i.e., the bioderived based plasticizer).

One skilled in the art will appreciate that a trace amount of DCC and/or DCU may remain in the bioderived based plasticizer in accordance with some embodiments of the present invention, even after purification. Detection of the presence of a trace amount of DCC and/or DCU in a sample of bioderived based plasticizer (or in a sample of the polymer into which the bioderived based plasticizer has been blended) may be indicative that the bioderived based plasticizer was prepared in accordance with some embodiments of the present invention.

In accordance with some embodiments of the present invention, an admixture may be produced by blending the bioderived based plasticizer into a polymer using techniques well known to those skilled in the art. The polymer may be any suitable polymer. Suitable polymers include, without limitation, polyvinyl chloride (PVC), polyvinylidene chloride (PVDC), polyacrylates, more particularly polymethyl methacrylate (PMMA), polyalkyl methacrylate (PAMA), fluoropolymers, more particularly polyvinylidene fluoride (PVDF), polytetrafluoroethylene (PTFE), polyvinyl acetate (PVAc), polyvinyl alcohol (PVA), polyvinyl acetals, more particularly polyvinyl butyral (PVB), polystyrene polymers, more particularly polystyrene (PS), expandable polystyrene (EPS), acrylonitrile styrene acrylate (ASA), styrene-acrylonitrile (SAN), acrylonitrile butadiene styrene (ABS), styrene-maleic anhydride copolymer (SMA), styrene-methacrylic acid copolymer, polyolefins, more particularly polyethylene (PE) or polypropylene (PP), thermoplastic polyolefins (TPO), polyethylene vinyl acetate (EVA), polycarbonates, polyethylene terephthalate (PET), polybutylene terephthalate (PBT), polyoxymethylene (POM), polyamide (PA), polyethylene glycol (PEG), polyurethane (PU), thermoplastic polyurethane (TPU), polysulfides (PSu), biopolymers, more particularly polylactic acid (PLA), polyhydroxybutyral (PHB), polyhydroxyvaleric acid (PHV), polyesters, starch, cellulose and cellulose derivatives, more particularly nitrocellulose (NC), ethylcellulose (EC), cellulose acetate (CA), cellulose acetate butyrate (CAB), rubber or silicones, and also mixtures or copolymers of the stated polymers or their monomeric units.

The loading level of the bioderived based plasticizer within admixture will vary depending on the application and the polymer. In accordance with some embodiments of the present invention, based on 100 parts by mass of the polymer, the admixture preferably contains from 1 to 100, and more preferably from 2 to 50, parts by mass of the bioderived based plasticizer.

One skilled in the art will appreciate that many variations are possible within the scope of the present invention. Thus, while the present invention has been particularly shown and described with reference to preferred embodiments thereof, it will be understood by those skilled in the art that these and other changes in form and details may be made therein without departing from the spirit and scope of the present invention.

What is claimed is:

1. A bioderived based plasticizer, comprising:
a reaction product of a bioderived diol and a bioderived carboxylic acid in the presence of N,N'-dicyclohexylcarbodiimide (DCC), wherein the bioderived carboxylic acid includes a hydrolyzed oil.

2. The bioderived based plasticizer as recited in claim 1, wherein the bioderived diol is selected from the group consisting of 2,5-bis(hydroxymethyl)furan, 2,5-bis(hydroxymethyl)-tetrahydrofuran, isosorbide, and mixtures thereof.

3. The bioderived based plasticizer as recited in claim 1, wherein the bioderived carboxylic acid includes a hydrolyzed oil having a chemical structure represented by the following formula:

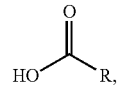

wherein R is aliphatic and contains from 5 to 25 carbon atoms.

4. The bioderived based plasticizer as recited in claim 3, wherein the bioderived carboxylic acid includes a hydrolyzed oil selected from the group consisting of linoleic acid, α-linolenic acid, oleic acid, and mixtures thereof.

5. The bioderived based plasticizer as recited in claim 4, wherein the bioderived diol includes 2,5-bis(hydroxymethyl)furan.

6. The bioderived based plasticizer as recited in claim 1, wherein the reaction product has a chemical structure represented by the following formula:

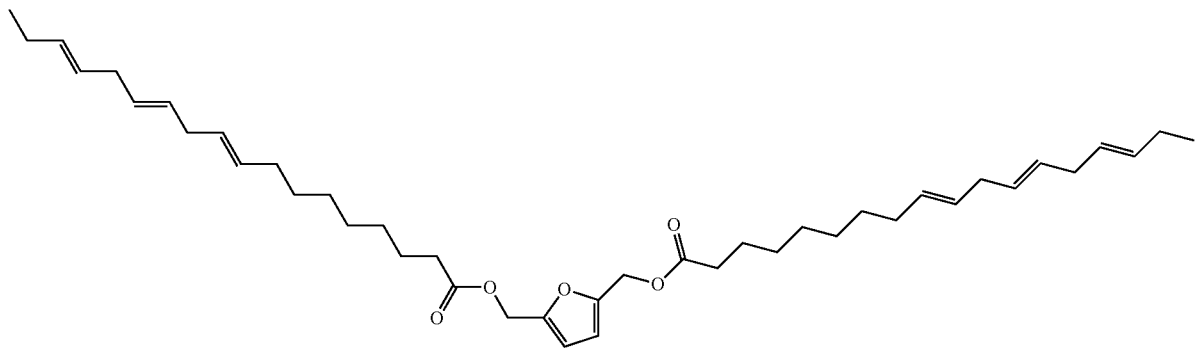 [SMILES: CC/C=C/C/C=C/C/C=C/CCCCCCCC(=O)OCc1ccc(COC(=O)CCCCCCC/C=C/C/C=C/C/C=C/CC)o1]

7. The bioderived based plasticizer as recited in claim 1, wherein the reaction product contains a trace amount of at least one of DCC and dicyclohexylurea (DCU).

8. A bioderived based plasticizer, comprising:
a reaction product of a bioderived diol and a bioderived carboxylic acid in the presence of N,N'-dicyclohexylcarbodiimide (DCC), wherein the bioderived diol is selected from the group consisting of 2,5-bis(hydroxymethyl)furan, 2,5-bis(hydroxymethyl)tetrahydrofuran, isosorbide, and mixtures thereof, and wherein the bioderived carboxylic acid includes a hydrolyzed oil selected from the group consisting of linoleic acid, α-linolenic acid, oleic acid, and mixtures thereof.

9. The bioderived based plasticizer as recited in claim 8, wherein the reaction product contains a trace amount of at least one of DCC and dicyclohexylurea (DCU).

10. A bioderived based plasticizer, comprising:
a reaction product of a bioderived diol and a bioderived carboxylic acid in the presence of N,N'-dicyclohexylcarbodiimide (DCC), wherein the bioderived diol is 2,5-bis(hydroxymethyl)furan, and wherein the bioderived carboxylic acid includes a hydrolyzed oil selected from the group consisting of linoleic acid, α-linolenic acid, oleic acid, and mixtures thereof.

11. The bioderived based plasticizer as recited in claim 10, wherein the hydrolyzed oil is α-linolenic acid, and wherein the reaction product has a chemical structure represented by the following formula:

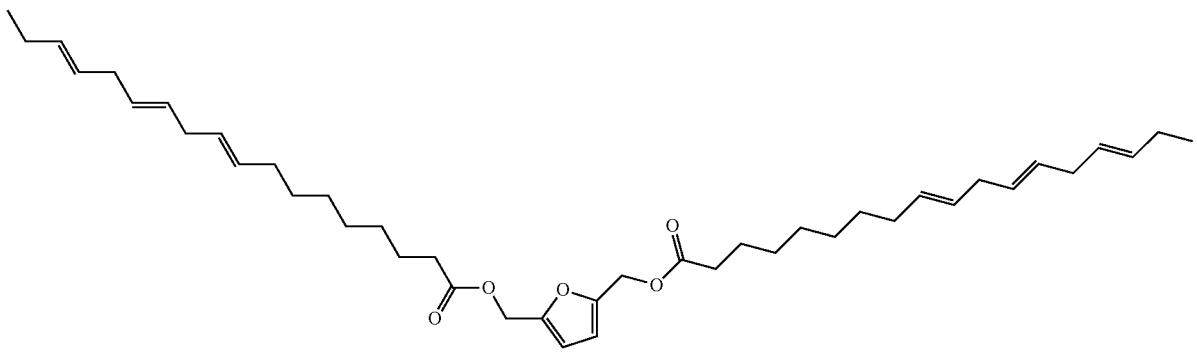 [SMILES: CC/C=C/C/C=C/C/C=C/CCCCCCCC(=O)OCc1ccc(COC(=O)CCCCCCC/C=C/C/C=C/C/C=C/CC)o1]

12. The bioderived based plasticizer as recited in claim 10, wherein the reaction product contains a trace amount of at least one of DCC and dicyclohexylurea (DCU).

* * * * *